(12) United States Patent
Young et al.

(10) Patent No.: US 11,259,580 B2
(45) Date of Patent: Mar. 1, 2022

(54) HEALTH MONITORING GARMENT AND SYSTEM

(71) Applicant: Cornerstone Research Group, Inc., Miamisburg, OH (US)

(72) Inventors: Trang T. Young, Dayton, OH (US); Mark C. Cridge, Miamisburg, OH (US); Scott A. Miller, Dayton, OH (US); Joshua E. Nieman, Centerville, OH (US); Gary N. Cupp, Washington Township, OH (US); Kristin M. Cable, Dayton, OH (US)

(73) Assignee: Cornerstone Research Group, Inc., Miamisburg, OH (US)

( * ) Notice: Subject to any disclaimer, the term of this patent is extended or adjusted under 35 U.S.C. 154(b) by 205 days.

(21) Appl. No.: 16/519,511

(22) Filed: Jul. 23, 2019

(65) Prior Publication Data

US 2020/0022431 A1    Jan. 23, 2020

Related U.S. Application Data

(60) Provisional application No. 62/701,960, filed on Jul. 23, 2018.

(51) Int. Cl.
*A61B 5/024* (2006.01)
*A41D 13/12* (2006.01)
(Continued)

(52) U.S. Cl.
CPC ........ *A41D 13/1281* (2013.01); *A61B 5/0002* (2013.01); *A61B 5/0053* (2013.01);
(Continued)

(58) Field of Classification Search
CPC ....... A61B 5/0002; A61B 5/0053; A61B 5/01; A61B 5/02055; A61B 5/14517; A61B 5/6804; A61B 5/02438; A61B 5/08
See application file for complete search history.

(56) References Cited

U.S. PATENT DOCUMENTS

| | | |
|---|---|---|
| 6,852,216 B2 | 2/2005 | Moscaritolo et al. |
| 7,559,902 B2 | 7/2009 | Ting et al. |
| | (Continued) | |

FOREIGN PATENT DOCUMENTS

| | | |
|---|---|---|
| CN | 204032410 U | 12/2014 |
| CN | 204207729 U | 3/2015 |
| | (Continued) | |

OTHER PUBLICATIONS

Lee et al. "Sensors and Actuators B: Chemical" ScienceDirect, Journals & Books, vol. 140, Issue 2, Jul. 16, 2009, 1 pg.
(Continued)

*Primary Examiner* — Allen Porter
*Assistant Examiner* — James Moss
(74) *Attorney, Agent, or Firm* — Dinsmore & Shohl LLP

(57) ABSTRACT

A health monitoring garment is provided. The health monitoring garment includes an article of clothing comprising at least one compression section to provide a snug fit against a person wearing the article of clothing and a sensor island. The sensor island includes stretchable circuitry, two or more sensors, one or more power supplies, and optionally one or more wireless communication modules within a self-contained unit. At least one of the sensors comprises a stretchable sensor which may be a respiration sensor. The sensor unit may be provided independent of the health monitoring garment or as a complete system. The sensor island and compression section of the article of clothing also include fasteners of complementary geometries for reversible attachment and disengagement of the sensor island from the compression section.

20 Claims, 7 Drawing Sheets

(51) Int. Cl.
*A61B 5/00* (2006.01)
*A61B 5/0205* (2006.01)
*A61B 5/01* (2006.01)
*A61B 5/145* (2006.01)
*A61B 5/08* (2006.01)

(52) U.S. Cl.
CPC ............ *A61B 5/01* (2013.01); *A61B 5/02055* (2013.01); *A61B 5/14517* (2013.01); *A61B 5/6804* (2013.01); *A61B 5/02438* (2013.01); *A61B 5/08* (2013.01); *A61B 2560/0214* (2013.01); *A61B 2562/0219* (2013.01); *A61B 2562/06* (2013.01)

(56) References Cited

U.S. PATENT DOCUMENTS

| | | |
|---|---|---|
| 9,895,105 B2 | 2/2018 | Romem |
| 2002/0032386 A1* | 3/2002 | Sackner ............... A61B 5/0205 600/536 |
| 2003/0212319 A1* | 11/2003 | Magill ................... A61B 5/25 600/382 |
| 2006/0117805 A1 | 6/2006 | Valentine et al. |
| 2007/0299325 A1* | 12/2007 | Farrell ................. A61B 5/6805 600/301 |
| 2009/0234262 A1 | 9/2009 | Reid, Jr. et al. |
| 2010/0185076 A1* | 7/2010 | Jeong ....................... A61B 5/25 600/388 |
| 2012/0136231 A1 | 5/2012 | Markel |
| 2013/0225966 A1 | 8/2013 | Macia Barber et al. |
| 2013/0245388 A1 | 9/2013 | Rafferty et al. |
| 2013/0274587 A1* | 10/2013 | Coza ................... A61B 5/6804 600/409 |
| 2013/0281795 A1 | 10/2013 | Varadan |
| 2014/0012145 A1* | 1/2014 | Kurzweil ............ A61B 5/6804 600/483 |
| 2014/0142459 A1 | 5/2014 | Jayalth et al. |
| 2014/0206948 A1 | 7/2014 | Romem |
| 2015/0335288 A1* | 11/2015 | Toth ..................... A61B 5/6833 600/373 |
| 2016/0263395 A1 | 9/2016 | Siegel et al. |
| 2016/0270700 A1* | 9/2016 | Baxi .................... A61B 5/1121 |
| 2016/0278651 A1 | 9/2016 | Lu et al. |
| 2016/0322283 A1* | 11/2016 | McMahon .......... H01L 21/4864 |
| 2017/0215800 A1* | 8/2017 | Chen ................... A61B 5/6831 |
| 2017/0258402 A1* | 9/2017 | Acquista ................. A61B 5/25 |
| 2017/0265810 A1 | 9/2017 | Van De Vyver |
| 2018/0184735 A1 | 7/2018 | Longinotti-Buitoni et al. |
| 2018/0184921 A1* | 7/2018 | Baxi ....................... A61B 5/352 |
| 2018/0199635 A1* | 7/2018 | Longinotti-Buitoni ..................... H01R 33/92 |
| 2019/0029566 A1* | 1/2019 | Sundaram ............ A61B 5/4833 |

FOREIGN PATENT DOCUMENTS

| | | |
|---|---|---|
| CN | 207461432 U | 6/2018 |
| EP | 1506738 A1 | 2/2005 |
| GB | 2350193 A | 11/2000 |
| JP | 6342596 B1 * | 6/2018 |

OTHER PUBLICATIONS

Schlosser et al. "Textile and Clothing Applications for Health Monitoring of Athletes and Potential Applications for Athletes with Disabilities" TATM Journal of Textile and Apparel, Technology and Management, vol. 8, Issue 1, Spring 2013, 25 pgs.

Soh "Wearable Wireless Health Monitoring: Current Developments, Challenges, and Future Trends" Article, Research Gate, May 2015, 25 pgs.

International Search Report and Written Opinion issued by the U.S. Patent and Trademark Office acting as International Searching Authority for Application No. PCT/US19/042984 dated Oct. 18, 2019 (13 pages total).

* cited by examiner

HEALTH MONITORING GARMENT AND SYSTEM

CROSS-REFERENCE TO RELATED APPLICATIONS

This application claims priority to U.S. Provisional Application 62/701,960, filed Jul. 23, 2018, which is incorporated by reference herein in its entirety.

STATEMENT REGARDING FEDERALLY SPONSORED RESEARCH OR DEVELOPMENT

This invention was made with U.S. Government support under Contract No. W81XWH-17-C-0115 and W81XWH-18-C-0093 awarded by U.S. Army to Cornerstone Research Group Inc. The U.S. Government has certain rights in the invention.

TECHNICAL FIELD

Embodiments of the present disclosure generally relate to health monitoring garments and systems.

BACKGROUND

Workers in arduous field conditions such as fire crews, chemical disposal groups, or soldiers in theatre or training missions often endure adverse health effects due to greater exposure to heat strain threats. Data from measured vital signs and physiological conditions can be compiled to ascertain health status and provide actionable insights into a patient's well-being, thus enabling proactive intervention as needed in hospital, healthcare and home care environments.

Presently available health monitoring equipment is lacking. Commercially available body-worn systems provide monitoring, but struggle to provide both accuracy and comfort. Adhesive systems for attaching monitoring devices to a subject's body initially appear convenient, but require skin surface preparation and may cause skin irritation. Wrist-worn devices are convenient to use, but suffer from poor accuracy. Chest straps are more accurate, but have bulky electronic modules and are often uncomfortable to wear due to their extremely tight fitting to mitigate shifting of sensors during active physical motion. Current clothing type systems typically contain large electronic modules that are too bulky and intrusive to be comfortably worn under protective clothing, thus negating any realized benefits.

SUMMARY

As such, there are needs for health monitoring systems which provide both comfort and accuracy. The present disclosure provides a wearable health monitoring system that distributes various health monitoring sensors, including removable electronics strategically placed at one or more locations throughout a garment that comprises at least one compression or form-fitting section to mitigate the bulkiness of currently available products and the drawbacks of poor contact for data collection between the sensors and subject's body. In addition, it allows interchangeability and removability of different sensors placed within the garment for tailoring various health monitoring needs and to provide washability of the health monitoring garment.

Embodiments of the present disclosure relate to a health monitoring garment. The health monitoring garment comprises an article of clothing and a sensor island. The article of clothing comprises at least one compression section configured as a garment to provide a snug fit against a person wearing the article of clothing. The sensor island comprises two or more sensors, stretchable circuitry, one or more power supplies, and optionally one or more wireless communication modules within a self-contained unit. At least one of the two or more sensors comprises a stretchable sensor, such as a respiration sensor or sensor for measuring physiological movement around various joints. Further, the sensor island and the compression section comprise fasteners of complementary geometries for reversible attachment and disengagement of the sensor island from the compression section.

Embodiments of the present disclosure relate to a sensor island for placement in a health monitoring garment. The sensor island includes two or more sensors, stretchable circuitry, one or more power supplies, and optionally one or more wireless communication modules within a self-contained unit. The stretchable circuitry includes a planar, substantially wave-shaped region of flexible circuit board. At least one of the two or more sensors comprises a stretchable sensor. The sensor island also includes an encapsulation of the stretchable circuitry, the one or more power supplies, and the optional one or more wireless communication modules with an elastomeric material.

BRIEF DESCRIPTION OF THE DRAWINGS

The following detailed description of specific embodiments of the present disclosure can be best understood when read in conjunction with the following drawings, in which.

DETAILED DESCRIPTION

Embodiments of the present disclosure generally relate to health monitoring garments, systems, and the subcomponents thereof. Specifically, a wearable health monitoring system that leverages multi-modal, distributive sensing through an array of miniature, ultra-low power sensors to realize high accuracy while mitigating bulkiness and discomfort is disclosed here. The health monitoring garments and systems presently disclosed include integration of electronics into a compression garment through a removable sensor island that enables remote health monitoring of physiological data and generation of actionable information while preserving a wearer's ability for full-range of movement and physical performance.

Figure 1:
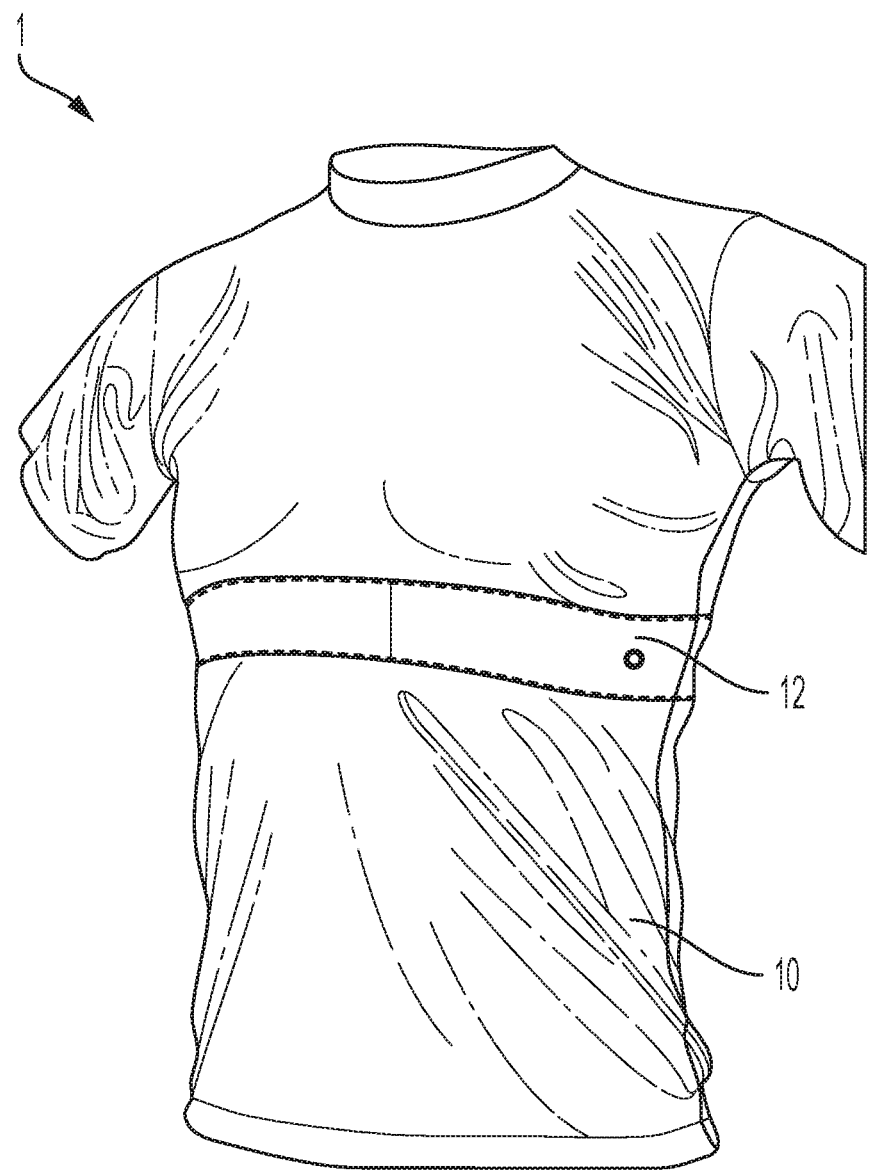
FIG. 1 is a health monitoring garment according to one or more embodiments of the present disclosure.
Figure 2:
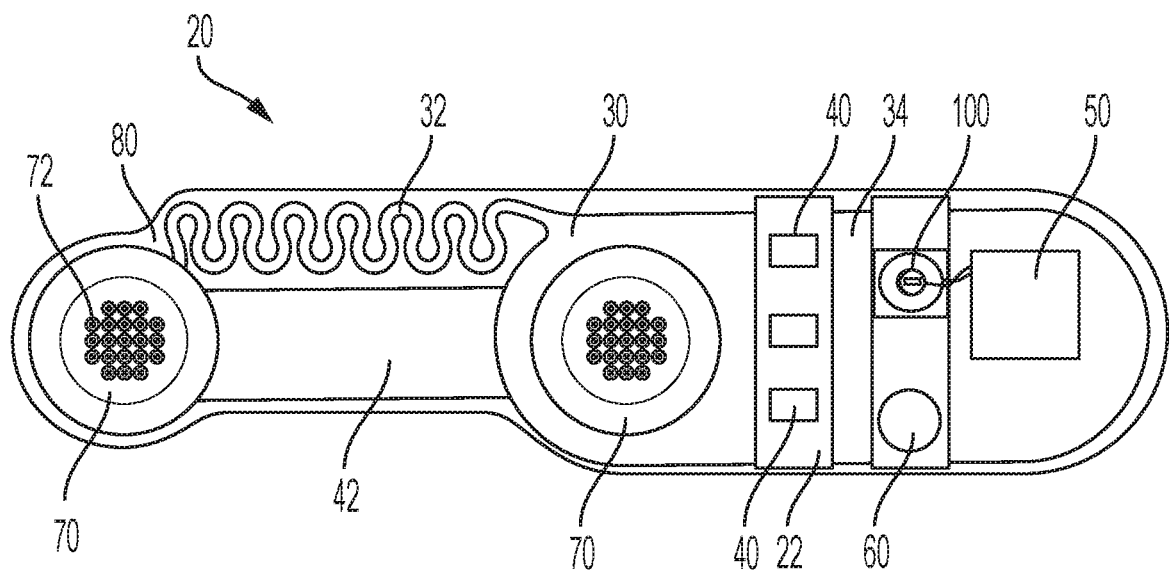
FIG. 2 is a sensor island according to one or more embodiments of the present disclosure.

In accordance with embodiments of a health monitoring garment, the health monitoring garment 1 comprises an article of clothing 10 and a sensor island 20. With reference to FIG. 1, the article of clothing 10 comprises at least one compression section 12 configured as a compression garment to provide a snug fit in at least one location against a person wearing the article of clothing 10. With reference to FIG. 2, the sensor island 20 comprises stretchable circuitry 30, two or more sensors 40, one or more power supplies 50, and optionally one or more wireless communication modules 60 within a self-contained unit. Further, at least one of the two or more sensors 40 comprises a stretchable sensor 42. The sensor island 20 and the compression section 12 also comprise fasteners of complementary geometries for reversible attachment and disengagement of the sensor island 20 from the compression section 12.

In various embodiments, the article of clothing 10 forming the health monitoring garment 1 may be a shirt, pants, undergarment, sock, or headwear based on the desired health parameters to be monitored with the sensors 40. For conciseness, the presented figures and description are focused on applications in a shirt, but it will be appreciated that usage may extend to any article of clothing.

In one or more embodiments, the stretchable sensor 42 is a respiration sensor comprising a stretchable construction that stretches in coordination with the wearer's breathing. The stretchable sensor 42 is sensitive to stretch and as such converts the expansion and contraction of the rib cage or abdominal area, to a rise and fall of a signal indicative of the wearer's breathing pattern. Data processing known to those skilled in the art allows for determination of the respiration rate of the wearer based on an output signal from the stretchable sensor 42. In one or more embodiments, the stretchable sensor 42 is capable of determination of both rate and depth/volume of breathing.

In one or more embodiments, the stretchable sensor 42 is formed from a stretchable strain sensor that has variable electrical capacitance based on the degree of induced strain from stretching the stretchable sensor 42. Specifically, the stretchable sensor 42 may comprise an electroactive polymer (EAP) thin films set in a silicone elastomer substrate. The stretchable sensor 42 when implemented as a respiration sensor is anticipated to stretch and contract back during each respiration which correlates to a change in electrical capacitance of the stretchable sensor 42 and can be algorithmically converted to a pattern of respiration. The stretchable sensor 42 may be formed from a stretchable dielectric layer sandwich between two thin EAP films with the whole assembly encapsulated by silicone elastomer. Each EAP layer is connected to a circuit separately for effecting a voltage difference across the dielectric layer. When a stretchable sensor 42 of such construction is stretched, the dielectric layer thins out and the capacitance increases between the two EAP film to provide the desired signal. Alternatively, the stretchable sensor may comprise a thin film piezoresistive semi-conductor with variable resistance dependent on strain. In one or more embodiments, the stretchable sensor 42 may comprise a profile of 10 by 50 mm and have a thickness of approximately 1.4 mm. It will be appreciated that in one or more embodiments, the stretchable sensor 42 may comprise a longest dimension up to the entire chest circumference of the wearer for measurement of respiration.

Sensor islands 20 may be tailored to target specific biometrics with each sensor island 20 comprising an integration of multiple sensors 40 configured for the specific biometrics of interest. The sensor island 20 includes a stretchable sensor 42 as previously indicate, but may also include one or more further sensors 40 such as a heart rate sensor, a sweat sensor, a temperature sensor, and an accelerometer.

In one or more embodiments, the sensors 40 include a heart rate sensor. The heart rate sensor is configured to monitor the heart rate of the wearer of the health monitoring garment 1. The heart rate of the wearer may be monitored with an indirect optics-based heart rate sensor. For example, indirect optics-based heart rate sensor may determine heart-rate data (pulse) through photoplethysmography (PPG), the process of using light to measure blood flow and oxygen level in the blood. Generally, optical heart-rate monitors have small light emitting diodes (LEDs) which shine green light onto the skin of the wearer. The different wavelengths of light from these optical emitters interact with the blood flowing through the dermis of the skin and the reflected and refracted light from the flowing blood therein is captured by an optical receiving sensor. Data processing known to those skilled in the art allows for determination of the pulsation of blood flow and thereby the heart rate of the wearer.

In one or more embodiments, the sensor island 20 may include a heart rate sensor capable of monitoring the electrical signals of the heart. Specifically, the heart rate sensor may comprise electrocardiogram (ECG) capabilities to provide the electrical signals of the heart muscle in addition to a basic heart rate. An ECG produces a recording of voltage versus time of the electrical activity of the heart using electrodes placed on the skin. These electrodes detect the small electrical changes that are a consequence of cardiac muscle depolarization followed by repolarization during each cardiac cycle or heartbeat. As such, in one or more embodiments, the sensors 40 include at least two dry electrodes 70 which may be utilized for acquisition of ECG measurements. Recordation of an ECG pattern allows for determination of a variety of cardiac abnormalities, including cardiac rhythm disturbances such as atrial fibrillation and ventricular tachycardia, inadequate coronary artery blood flow such as myocardial ischemia and myocardial infarction, and electrolyte disturbances such as hypokalemia and hyperkalemia.

Figure 3:
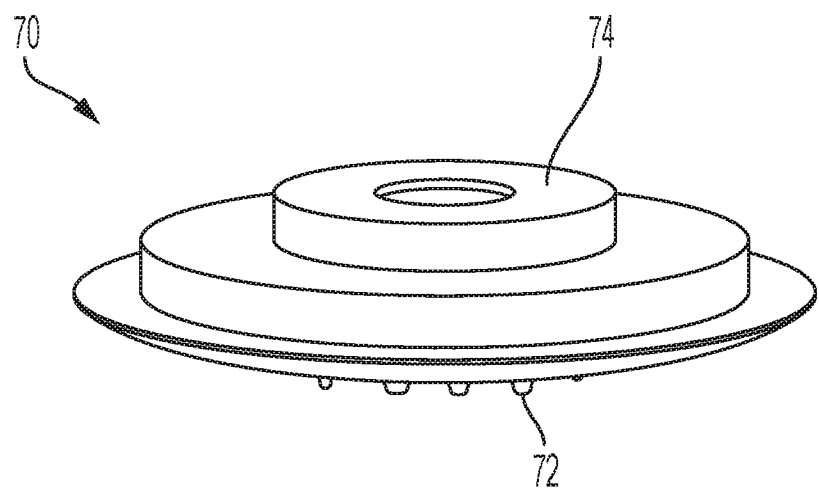
FIG. 3 is a dry electrode according to one or more embodiments of the present disclosure.

In one or more embodiments, the dry electrodes 70 do not require any skin preparation or conductive gel to be employed as a component for the heart rate sensor. Generic dry electrodes 70 are commercially available, for example from Orbital Research Inc. (Cleveland, Ohio). With reference to FIGS. 2 and 3, the dry electrodes 70 may include bumps or surface features 72 that are compressible to improve contact with the skin. The bumps or surface features 72 help to hold the dry electrodes 70 in place which minimizes artifacts in the data due to body motion. The surface features 72 may also dig through the outermost dead skin layer (i.e. stratum corneum) to achieve contact with the electrical signals underneath the stratum corneum for accurate measurement. In one or more embodiments, the dry electrodes 70 are made with silver/silver chloride coated ABS (acrylonitrile butadiene styrene).

In one or more embodiments, the sensors 40 include a sweat or perspiration sensor. Measurement of the presence of perspiration or sweat from the wearer of the health monitoring garment 1 allows the wearer to be monitored for dehydration conditions. It will be appreciated that changes in the rate or presence of perspiration during physical exertion may be correlated to dangerous dehydration conditions with a decrease or termination of sweating indicative of a concerning state. In one or more embodiments, the perspiration sensor be positioned to absorb and collect sweat samples for determination of the presence of potential biomarkers.

In one or more embodiments, the sensors 40 include a temperature sensor. The temperature sensor may be configured to establish the skin temperature of the wearer of the health monitoring garment 1. Determination of the wearer's skin temperature may provide the benefit of monitoring the wearer for conditions associated with overheating during physical exertion. In one or more embodiments, the temperature sensor may be sensitive to a temperature range of −55° C. to 130° C., and preferably 25° C. to 45° C. with an accuracy of ±0.05° C. or ±1.5° C. In various embodiments, the temperature sensor may be provided in a package having a footprint of approximately 2 mm by 1.25 mm, 1.5 mm by 1.25 mm, or 1 mm by 1 mm. The temperature sensor may be a CMOS integrated-circuit temperature sensor such as the LM20 analog temperature sensor commercially available from Texas Instruments (Dallas, Tex.).

In one or more embodiments, the sensors 40 include an accelerometer or motion sensor. The accelerometer provides the capability for the health monitoring garment 1 to track positioning and movement of the wearer of the health monitoring garment 1. Determination of the positioning or movement of the wearer may be combined with data acquisitions from one or more other sensors 40 to provide a more reasoned analysis of the wearer's health by accounting for the level of exertion or physical orientation of the wearer. The accelerometer provides record of motion including potential events related to wearer's balance or stance. In various embodiments, the accelerometer may be provided in a package having a footprint of approximately 1.6 mm by 1.6 mm or less than 3 square millimeters ($mm^2$) or a volume of 2.5 mm by 3.0 mm by 0.83 mm. Potential motion sensors include a combination accelerometer and gyroscope such as the ISM330DLC commercially available from STMicroelectronics (Geneva, Switzerland).

The sensor island 20 comprises stretchable circuitry 30 which may connect two or more of the sensors 40. In one or more embodiments the stretchable circuitry 30 comprises at least one planar, substantially wave-shaped region 32. Such wave-shape region may be made from a flexible but non-stretchable substrate with a metal trace adhered on it. Alternatively, such wave-shape region may be made from a flexible/stretchable conductive ink printed on a stretchable elastomer substrate. The wave-shaped region 32 allows the stretchable circuitry 30 to be reversibly elongated by extension of the wave-shaped pattern despite the non-stretchable nature of the flexible substrate or relatively lower strain limit of the flexible/stretchable ink. An overall strain capacity of 25% strain may be achieved with such wave-shape without degrading the electronic performance of the circuit and the sensor island 20. It will be appreciated that that wave-shaped region 32 provides an artificially extended electrical pathway which allows the ends of the wave-shaped region 32 to be moved apart without breaking the electrical pathway.

In various embodiments, the stretchable circuitry 30 is formed with a polyimide or poly-ether-ether-ketone (PEEK) substrate which provides flexibility to the stretchable circuitry 30. Specifically, the stretchable circuitry 30 can be flexed or folded which allows the stretchable circuitry 30 to conform to the contours of the body of the wearer of the health monitoring garment 1. The flexibility of the stretchable circuitry 30 also allows the wave-shaped region 32 to be extended as each loop of the wave-shaped region 32 is deformed during extension.

The electronic traces on the stretchable circuitry 30 should be selected to withstand the flexion of the stretchable circuitry 30 during repeated placement and utilization within the health monitoring garment 1. Specifically, in one or more embodiments, the electronic traces may comprise a metallic foil encapsulated by a flexible polyimide overlay, thus making the electronic traces capable of being repeatedly flexed without breakage. In various embodiments, the metallic foil forming the electronic traces may comprise copper (Cu), gold (Au), silver (Ag), or platinum (Pt).

In one or more embodiments, the stretchable circuitry 30 may be formed with flexible/stretchable conductive inks. The conductive inks may be applied in a wave-shape pattern to a stretchable substrate such as silicone, thermoplastic polyurethane (TPU), or thermoplastic elastomer (TPE). The flexible/stretchable conductive ink can be stretchable up to a strain of 5% without degrading the conductivity performance, but by printing it in wave-shape pattern on an elastomeric substrate, the overall circuitry may have far greater strain capacity of up to 25%. The conductive ink allows for flexion and stretching of the electronic traces connecting the sensors 40. A commercially available stretchable electronic ink is the Intexar™ line of stretchable electronic inks from DuPont Microcircuit Materials (Research Triangle Park, N.C.).

The sensors 40, power supply 50, and optional wireless communication module 60 are each affixed and in electrical connection to the stretchable circuitry 30. In one or more embodiments, the wave-shaped region 32 of the stretchable circuitry is positioned between the dry electrodes 70 and a flexible circuit board region 34 is provided beyond one of the dry electrodes 70 for affixing one or more of the sensors 40, the power supply 50, the optional wireless communication module 60, and other electronic hardware, such as micro-processors, memory chips, voltage regulator.

In one or more embodiments, the sensor island 20 comprises a rigid spline 22 in alignment with a location of fixation of one or more sensors 40 or other electronic hardware, such as micro-processors, memory chips, voltage regulator, to the stretchable circuitry 30 and the flexible circuit board region 34. The connection between the sensors 40 or other hardware and the stretchable circuitry 30 may be compromised if the stretchable circuitry 30 is stretched or flexed at the point of connection. Specifically, the sensors 40 or other hardware are generally rigid in the form of a chip and are not capable of flexion or stretching resulting in stress concentration at the junction with the stretchable circuitry 30 if the stretchable circuitry 30 is flexed or stretched. To overcome this challenge, the sensor island 20 may comprise one or more rigid splines 22 at the points of fixation of the sensors 40 or other hardware. The rigid spline 22 acts as a strain relief for the connection between the flexible circuitry and the one or more electronic components such as the integrated circuit chips or sensors 40. The rigid splines 22 comprise an inflexible substrate affixed to or placed adjacent the stretchable circuitry 30 to shield the connection between the sensors 40 or other hardware and the flexible circuitry from any externally induced stretching or flexion forces.

In one or more embodiments, the rigid splines 22 comprise an elongated geometry and are placed within the sensor island 20 such that the sensor island 20 as a whole retains an ability to conform to a wearer's profile. Specifically, the rigid splines 22 may be provided as one or more ribs extending in a direction perpendicular to the anticipated direction of stretching forces applied to the sensor island 20. One or more sensors 40 or other hardware may be positioned in alignment with each rib allowing for flexion of the sensor island 20 and the stretchable circuitry 30 in spaces between the ribs, but retaining rigidity in alignment with the ribs.

In one or more embodiments, the sensor island 20 comprises an encapsulation of the stretchable circuitry 30, the sensors 40, the one or more power supplies 50, and the optional one or more wireless communication modules 60 with an elastomeric material to form encapsulated circuitry. In various embodiments, the elastomeric material comprises silicone, TPU, or TPE.

Encapsulation of the stretchable circuitry 30, the power supply 50, and the optional wireless communication module 60 with the elastomeric material allows for the overall stretchability of the sensor island 20 and provides protection to the components of the sensor island 20. Specifically, the elastomeric encapsulation 80 provides a barrier to protect the components of the sensor island 20 from sweat and other moisture encountered during operational use. The elastomeric encapsulation 80 also provides protection against physical damage to the sensor island components from impacts or other forcible trauma encountered during rugged applications.

Figure 4:
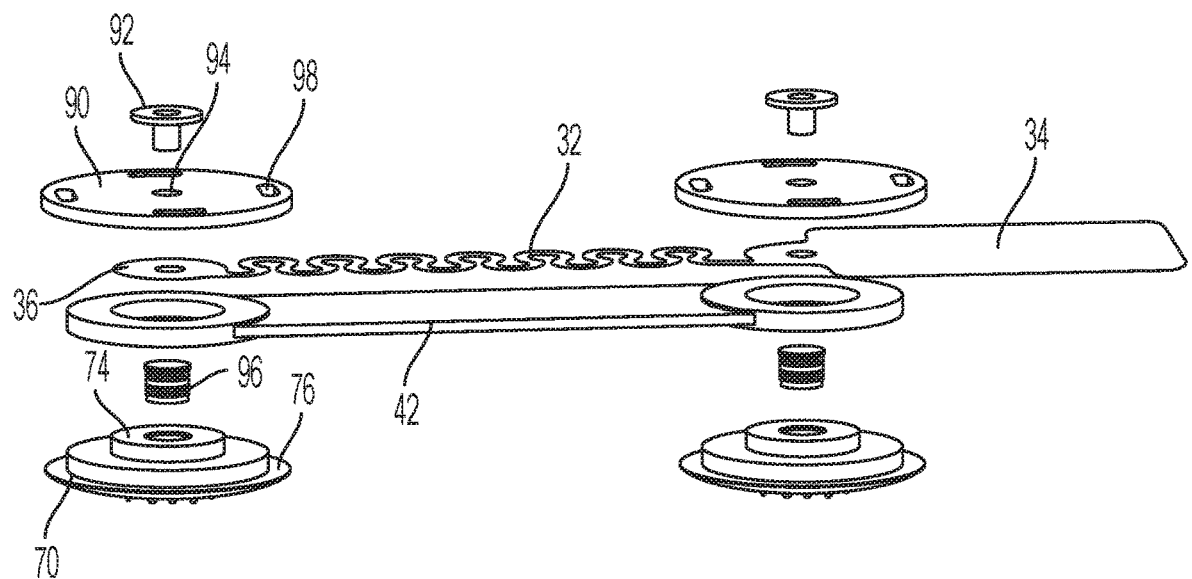
FIG. 4 is an exploded view of a sensor island according to one or more embodiments of the present disclosure.

With reference to FIG. 4, in one or more embodiments, the stretchable circuitry 30 comprises a region of un-encapsulated electrical contacts 36 configured to electrically mate with the dry electrodes 70 during assembly of the sensor island 20. The electrical contacts 36 are exposed through the elastomeric encapsulation 80 to allow electrical connection and contact with a mating surface 74 of the dry electrodes 70.

Figure 5:
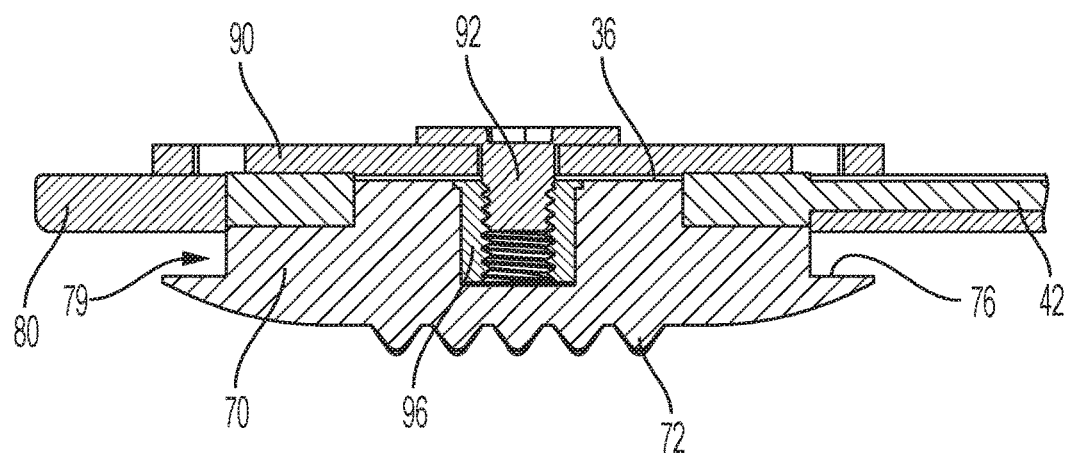
FIG. 5 is a cross-sectional view of the sensor island of FIG. 4 in an assembled configuration.
Figure 6:
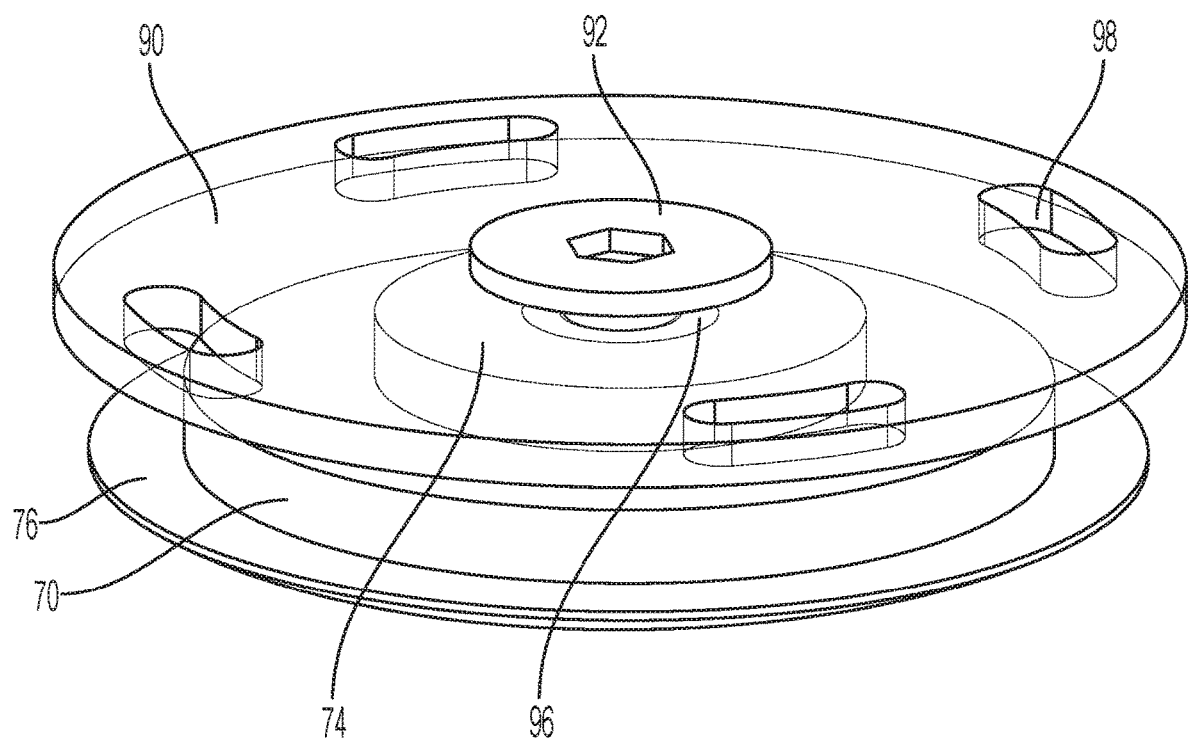
FIG. 6 is an assembly of a mounted dry electrode according to one or more embodiments of the present disclosure.

In one or more embodiments, the dry electrodes 70 may be affixed to the sensor island 20 with a threaded connection. With reference to FIGS. 4, 5, and 6, after encapsulating the stretchable circuit 30, the other sensors 40, and other electronic components with elastomeric encapsulation 80, a retention washer 90 may be placed on a first side of the encapsulation 80 with a male threaded fastener 92, such as a wafer head fastener, passed through a central hole 94 in the retention washer 90. A threaded insert 96 with female threads complementary to the male threaded fastener 92 may be affixed within the dry electrodes 80. In one or more embodiments, the threaded insert 96 may comprise brass, plastic or other metal. It will be appreciated that the threaded insert 96 may be a separate component than the dry electrode 70 or may be integrally formed as part of the housing of the dry electrode 70. Subsequently, the dry electrodes 70 may be affixed to the sensor island 20 by matching the male threaded fastener 92 and the threaded insert 96. The threaded connection allows the dry electrode 70 to be snuggly attached to the sensor island 20 to form a robust connection between the electrical contacts 36 on the stretchable circuitry 30 and the electrical contacts on the mating surface 74 of the dry electrodes 70. It will be appreciated that the male threaded fastener 92 is discussed as having a male thread and the threaded insert 96 is discussed as having a female thread, but it is conceived that the male threaded fastener 92 may comprise a female thread and the threaded insert 96 may comprise a male thread.

In one or more embodiments, the retention washer 90 may comprise one or more orifices 98 positioned around the periphery.

In one or more embodiments, the stretchable sensor 42 may extend between the dry electrodes 70. Specifically, the stretchable sensor 42 may be positioned with the ends of the stretchable sensor 42 aligned with the dry electrodes 70 such that the stretchable circuitry 30 produced with stretchable conductive ink and the stretchable sensor 42 are stacked as illustrated in FIG. 4. Stacking the stretchable sensor 42 and the stretchable circuitry 30 reduces the footprint of the sensor island 20 by routing multiple components along the same pathway. In further embodiments, the stretchable circuitry 30 may extend between the dry electrodes offset from the pathway of the stretchable sensor 42 as illustrated in FIG. 2. Further, as illustrated in FIGS. 4 and 5, the stretchable sensor 42 may include an overmolded washer to retain the stretchable sensor 42 in position.

In one or more embodiments, the power supply 50 comprises a thin film battery such as a thin film lithium battery. The power supply 50 may be positioned on the stretchable circuitry 30 in a distinct region from the sensors 40. In further embodiments, the thin film battery forming the power supply 50 may be a rechargeable thin film battery such as a thin film rechargeable battery.

In one or more embodiments, the sensor island 20 may further comprise a recharging port (not shown) accessible through the elastomeric encapsulation 80 electrically connected to the rechargeable battery. The rechargeable thin film battery forming the power supply 50 may be recharged through the recharging port using a power source external to the sensor island 20 when the health monitoring garment 1 is not in use. The recharging port may comprise a standard interface, such as USB, 4-pin connectors, or single prong.

In one or more embodiments, the sensor island 20 may further comprise a wireless charging circuit 100 connected to the rechargeable thin film battery forming the power supply 50. The wireless charging circuit 100 allows the rechargeable thin film battery to be recharged while encapsulated within the elastomeric encapsulation 80. Charging with the wireless charging circuit 100 may operate under the principles of inductive charging. Inductive charging uses an electromagnetic field to transfer energy using electromagnetic induction, the production of electricity across a magnetic field. An induction coil is used to create an alternating electromagnetic field from within a charging station (transmitter), and a second induction coil in the wireless charging circuit (receiver) receives power from the electromagnetic field, rectifies the voltage, and regulates electric current to charge the battery. Specifically, the two induction coils in proximity combine to form an electrical transformer.

It will be appreciated that multiple sensor islands 20 with the same or different configurations may be strategically placed on the article of clothing 10. A plurality of sensor islands 20 allows the health monitoring garment 1 to provide redundant measurement for cross-checking of collected data as well as position sensors 40 in the optimum position for the specific sensor type. Further, utilization of a plurality of sensor islands 20 also allows the sensor islands 20 to be reduced in size and reduce the likelihood of the wearer experiencing discomfort or reduction in mobility as a result of the health monitoring garment 1.

In one or more embodiments, the health monitoring garment 1 includes one or more wireless communication modules 60. The wireless communication modules 60 serve to transmit data collected from the individual sensors 40 on the sensor island 20 to an external device for further processing, recording, or both. Specifically, the health monitoring garment 1 may use wireless communication protocols to enable multiple sensor islands 20 to communicate with each other, as well as communicate to the wearer's mobile device or other proximal external device. In one or more embodiments, one main sensor island 20 may be used to communicate with the mobile device or other receiving external device. Other sensor islands 20 may then send information to the main sensor island 20, so that the data can be transmitted to the external device as appropriate. Specifically, one sensor island 20 may serve as a master sensor island with data from the remaining sensor islands wirelessly transmitted thereto, the master sensor island communicating with the external device. The use of wireless communication such as near field communication protocol with RF at sub 1 GHz levels, eliminates the need to route interconnecting wires between sensor islands 20 that may present challenges in allowing comfort to wearer and providing durability to the health monitoring garment 1.

The sensor island 20 is prepared to maintain a low profile. In one or more embodiments, the sensor island 20 may comprise a thickness of less than or equal to 0.5 inches, less than 0.4 inches, or less than 0.35 inches in alignment with the dry electrodes 70. It will be appreciated that the area of the sensor island 20 in alignment with the dry electrodes 70 may be the thickest portion of the sensor island 20 as the dry electrodes 70 extend beyond the elastomeric encapsulation 80 to make contact with the wearer's skin. In one or more embodiments, the region of the sensor island 20 with the stretchable sensor 42 may comprise a thickness of less or equal to 0.1 inches, less than 0.08 inches, or less than 0.04 inches. In one or more embodiments, the region of the sensor island 20 with various sensors 40 affixed to the stretchable circuitry 30 in the chip region 34 may comprise a thickness of less than or equal to 0.3 inches, less than or equal to 0.2 inches, or less than or equal to 0.12 inches. In one or more embodiments, the region of the sensor island 20 in alignment with the power supply 50 may comprise a thickness of less or equal to 0.3 inches, less than or equal to 0.25 inches, or less than or equal to 0.2 inches.

Figure 7:
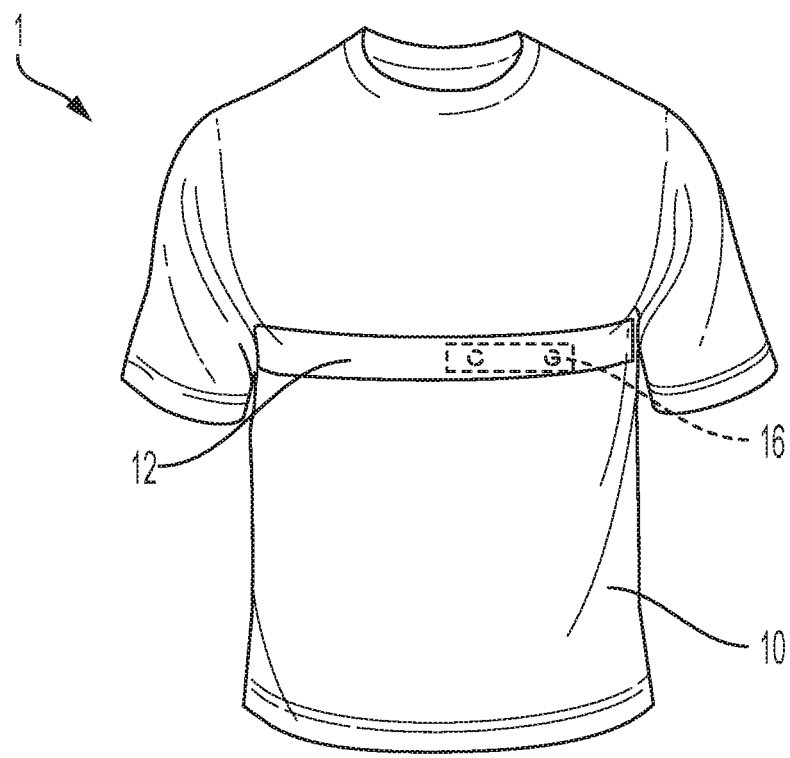
FIG. 7 is a health monitoring garment illustrating mounting of the sensor island with broken lines according to one or more embodiments of the present disclosure.

The article of clothing 10 comprises at least one compression section 12 configured as a compression garment to provide a snug fit against a person wearing the article of clothing 10. The compression section 12 may comprise at least one high power stretch band and may further comprise an additional section of intermediate power stretch band immediately below the high power stretch band, resulting in a gradient transition between high compression power to low compression power within the article of clothing 10. The rest of the article of clothing 10 may be formed from low power stretchable fabric to maintain a comfort fit against the wearer while still allowing freedom of movement such that the body movement at the region with "low power" fabric will not result in enough pulling force on the compression section 12 to interfere with the contact of the sensors with the wearer's body. The use of an intermediate power stretch band allows for more natural feel and less restrictive on blood flow thus better comfort for the wearer. It will be appreciated that "high power" and "low power" are provided as relative terms to illustrate the relative compressive force or elasticity exhibited by differing regions of the article of clothing and the exact magnitude of the compressive force may be selected in each case based on the specific needs of each application of the health monitoring garment 1. With reference to FIG. 7, in one or more embodiments, the compression section 12 comprises a pocket 14 formed within the article of clothing 10. The pocket 14 is sized to house the sensor island 20 and comprises orifices 16 to allow physical contact between the dry electrodes 70 and the skin of the person wearing the article of clothing 10.

In one or more embodiments, the pocket 14 may be formed as a tube sewn or otherwise affixed to either the interior or exterior of the article of clothing 10. As such, the pocket 14 may include two open ends allowing the sensor island 20 to be slid in from either open end and positioned in alignment with the orifices 16 that are open to the interior of the article of clothing 10. In further embodiments, the pocket 14 may be formed with a single open end, either from the top or the side, for inserting the sensor island 20 into the pocket 14.

The positioning of the sensor islands 20 may be selected to maximize accuracy and minimize impact of artifacts in the collected data due to body motion of the wearer. In one or more embodiments where the article of clothing 10 is a shirt, the compression section 12 may be located across the torso of the shirt such that the sensor island 20 may be positioned in proximity to the left pectoral muscle of the person wearing the shirt. The placement of the sensor island 20 at this particular location is to increase the accuracy of heart rate and respiration data from the heart rate sensor and stretchable sensor 42 respectively.

Figure 8:
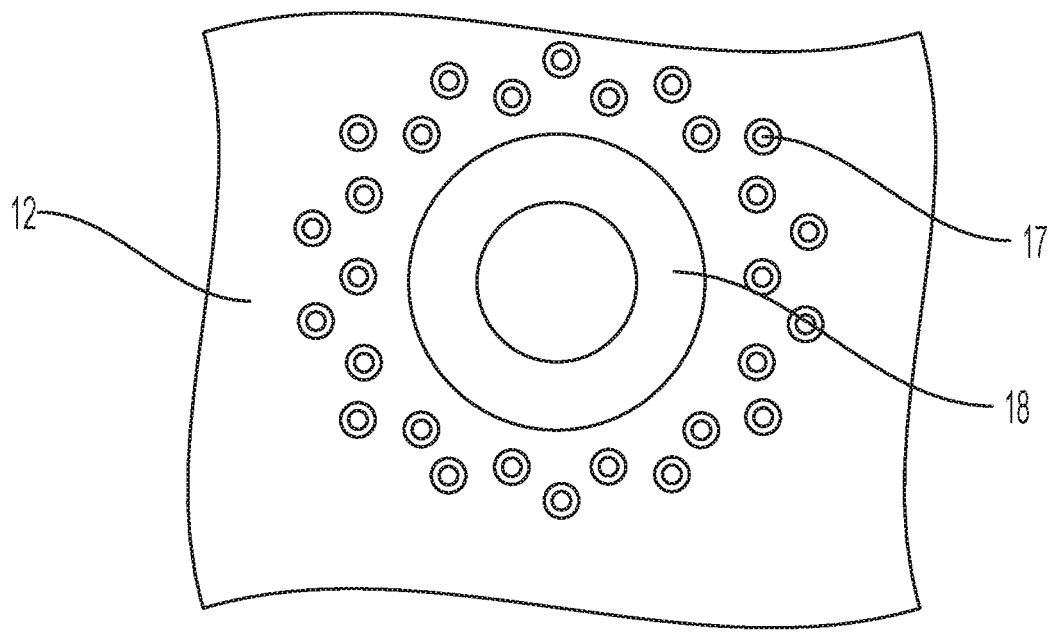
FIG. 8 is an illustration of an elastomeric material applied to the interior surface of the article of clothing proximal the sensor island according to one or more embodiments of the present disclosure.
Figure 9A:
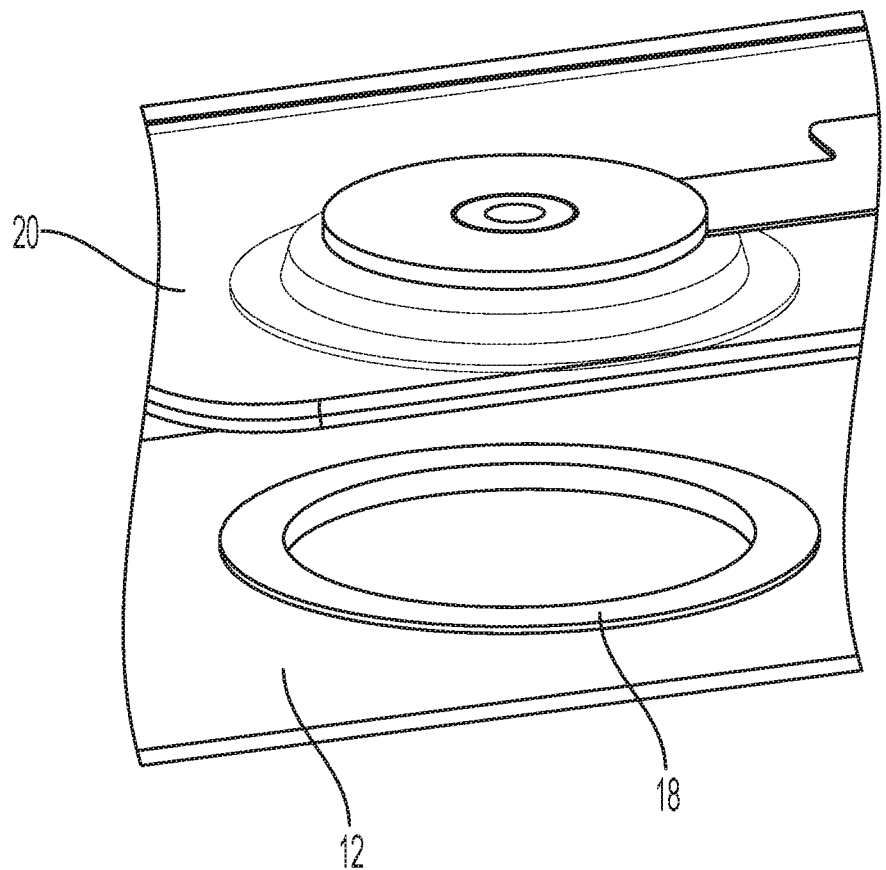
FIG. 9A is an illustration of a sensor island and compression section aligned for attachment according to one or more embodiments of the present disclosure.
Figure 9B:
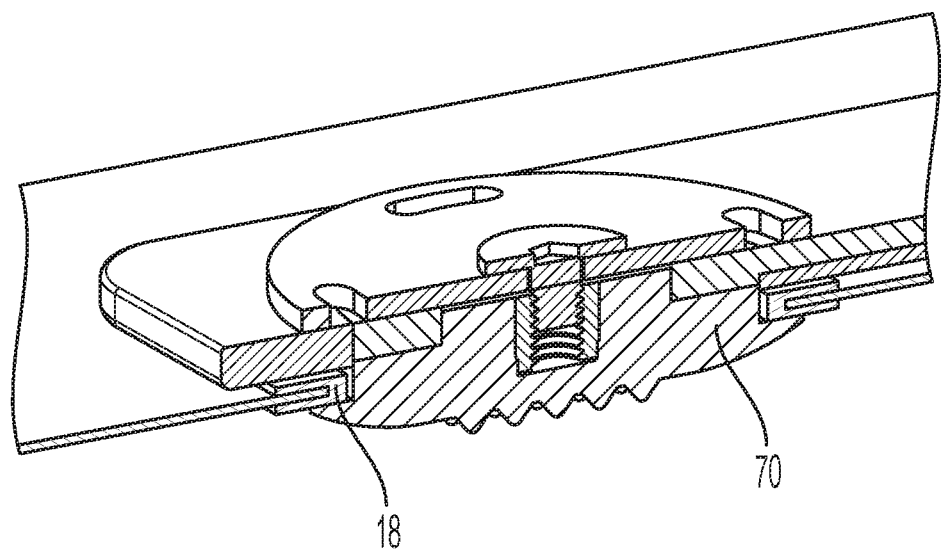
FIG. 9B is an illustration of the sensor island and compression section of FIG. 9A attached according to one or more embodiments of the present disclosure.

In one or more embodiments, the article of clothing 10 comprises anti-slip material bonded to an interior surface of the article of clothing 10 proximal the sensor island 20 within the compression section 12. The anti-slip material assists in retaining the compression section 12 and sensor island 20 in the desired position by providing a high friction connection between the wearer's skin and the compression section 12. In various embodiments, the anti-slip material may comprise silicone. In one or more embodiments, the anti-slip material may be applied as a continuous film over the entirety or only a portion of the compression section. In further embodiments, the anti-slip material may be applied in a discontinuous pattern. For example, the anti-slip material may be applied as a plurality of dots, a series of stripes, a grid, or other pattern. With reference to FIG. 8, the anti-slip material is applied as a series of dots 17 to the interior surface of the article of clothing 10 proximal the sensor island 20.

The sensor island 20 and the compression section 12 each comprise fasteners of complementary geometries for reversible attachment and disengagement of the sensor island 20 from the compression section 12. With reference to FIGS. 4, 5, 6, and 9A-9B, in one or more embodiments, the dry electrode 70 comprises an extended flange 76 around the periphery of the dry electrode 70. The extended flange 76 around the periphery of the dry electrode 70 and the encapsulated circuitry of the sensor island 20 form a recessed channel 79 sized to match and engage a complementary mating ring 18 provided within the structure of the compression section 12 of the article of clothing 10. The mating ring 18 is capable of being stretched in one or more directions such that the mating ring 18 may be placed within the recessed channel. The recessed channel 79 and the complementary mating ring 18 provide fasteners of complementary geometries and secure the sensor island 20 in place within the compression section 12.

The mating ring 18 is formed by reinforcing a substantially circular cutout within the structure of the material forming the compression section 12. In various embodiments, the reinforcement comprises stitching, an elastomeric coating, or an elastomeric insert such as a grommet.

Figure 10:
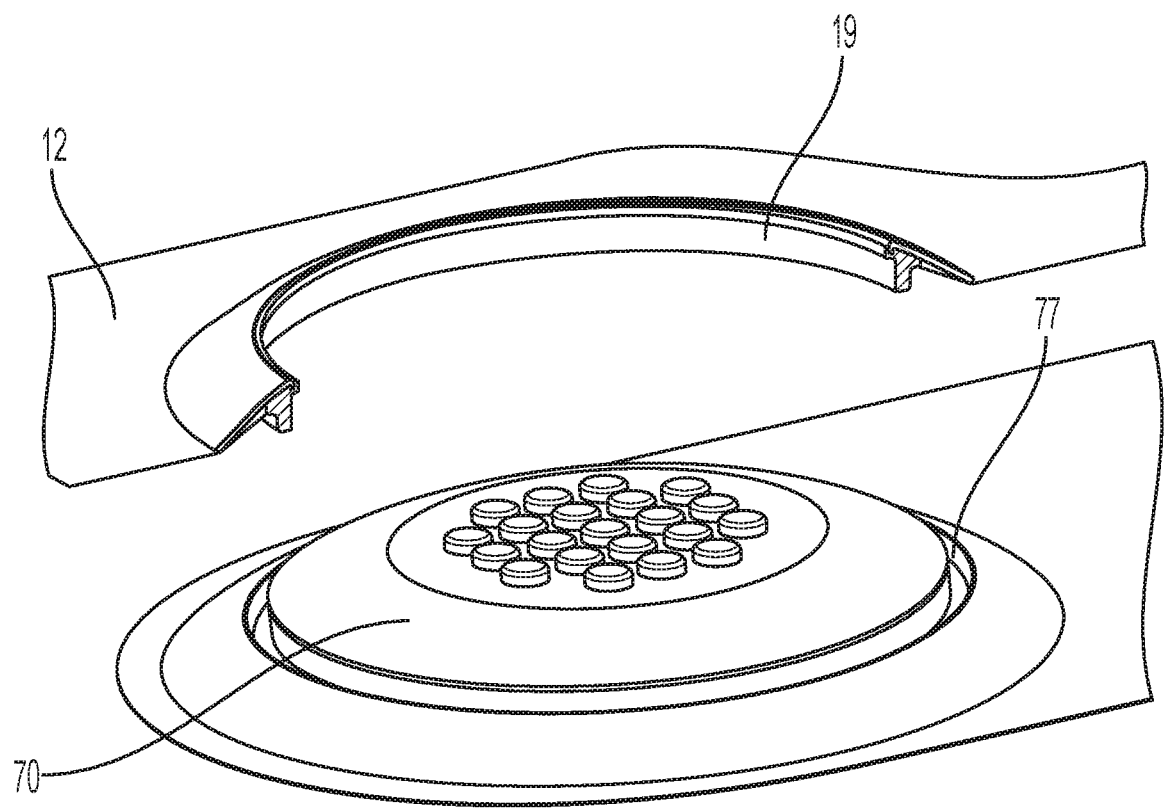
FIG. 10 is an illustration a sensor island and compression section aligned for attachment according to one or more embodiments of the present disclosure.

In one or more embodiments, the fasteners comprise at least one snap-on connector disposed within the dry electrode 70 and at least one mating snap-on connector disposed in the compression section 12 oriented toward an interior of the health monitoring garment 1. With reference to FIG. 10, a recessed groove 77 on the dry electrode 70 and a complementary mating snap ring 19 provides fasteners of complementary geometries and secure the sensor island 20 in place within the compression section 12.

As the sensor islands 20 are removable, they can be swapped out for a different type of sensor island 20 with a unique selection of sensors 40 or may be transferred to a different article of clothing 10. Such interchangeability allows for placement of a sensor island 20 which only includes the desired sensors 40 for a given application or scenario to both minimize bulkiness and maximize battery life. Further, the interchangeability of the sensor islands 20 allows for a single sensor island 20 to be used by a user in different uniforms within a military unit or firehouse for example, thereby minimizing inventory and equipment costs.

After removal of the sensor island 20 from the article of clothing 10, standard garment laundering practices can be used as the article of clothing 10 does not comprise any electronics, wiring, or other hardware susceptible to damage in a laundering procedure.

As the sensor island 20 and the article of clothing 10 are separate articles, standard manufacturing processes in garment and electronics industries can be leveraged for lower cost manufacturing. Further, the separate nature of the sensor island 20 and the article of clothing 10 allows one to be replaced due to wear or damage without requiring replacement of the entire system. For example, infliction of a tear in the article of clothing 10 does not require replacement of the entire health monitoring garment 1 including the sensor island 20 as the intact sensor island 20 may simply be utilized in a replacement article of clothing 10. Such swapping of components is not possible in systems which include monitoring components integrated or embedded within the garment such as wires or conductive fibers.

It should be understood that the various aspects of the health monitoring garment and a sensor island for placement in the same are described and such aspects may be utilized in conjunction with various other aspects.

In a first aspect, the disclosure provides a health monitoring garment. The health monitoring garment comprises an article of clothing having at least one compression section to provide a snug fit against a person wearing the article of clothing and a sensor island. The sensor island comprises two or more sensors, stretchable circuitry, and one or more power supplies within a self-contained unit. Further, at least one of the two or more sensors comprises a stretchable sensor. The sensor island and the compression section comprise fasteners of complementary geometries for reversible attachment and disengagement of the sensor island from the compression section.

In a second aspect, the disclosure provides the health monitoring garment of the first aspect, in which the sensor island further comprises an encapsulation of the stretchable circuitry and the one or more power supplies with an elastomeric material to form encapsulated circuitry.

In a third aspect, the disclosure provides the health monitoring garment of the second aspect, in which the sensor island further comprises one or more wireless communication modules within the self-contained unit and encapsulated with the elastomeric material.

In a fourth aspect, the disclosure provides the health monitoring garment of the second or third aspect, in which the elastomeric material comprises silicone.

In a fifth aspect, the disclosure provides the health monitoring garment of any of the first through fourth aspects, in which the two or more sensors comprise at least two dry electrodes connected by the stretchable circuitry.

In a sixth aspect, the disclosure provides the health monitoring garment of the fifth aspect, in which the stretchable circuitry comprises exposed electrical contacts configured to electrically mate with the dry electrodes.

In a seventh aspect, the disclosure provides the health monitoring garment of the fifth aspect, in which the dry electrode comprises an extended flange around the periphery of the dry electrode, the extended flange and the encapsulated circuitry of the sensor island form a recessed channel sized to engage a complementary mating ring provided within the structure of the compression section of the article of clothing, the recessed channel and the complementary mating ring providing the fasteners of complementary geometries.

In an eighth aspect, the disclosure provides the health monitoring garment of the fifth aspect, in which the compression section comprises a pocket formed within the article of clothing to house the sensor island, the pocket comprising orifices to allow physical contact between the dry electrodes and the skin of the person wearing the article of clothing.

In a ninth aspect, the disclosure provides the health monitoring garment of any of the first through eighth aspects, in which the one or more power supplies comprise a thin film battery.

In a tenth aspect, the disclosure provides the health monitoring garment of the ninth aspect, in which the thin film battery is a rechargeable thin film battery and the sensor island further comprises a wireless charging circuit connected to the rechargeable thin film battery.

In an eleventh aspect, the disclosure provides the health monitoring garment of any of the first through tenth aspects, in which the stretchable circuitry comprises a planar, substantially wave-shaped region.

In a twelfth aspect, the disclosure provides the health monitoring garment of any of the first through eleventh aspects, in which the one or more sensors further comprise one or more of a heart rate sensor, a sweat sensor, a temperature sensor, a gyroscope, and an accelerometer.

In a thirteenth aspect, the disclosure provides the health monitoring garment of any of the first through twelfth aspects, in which the stretchable sensor is a respiration sensor.

In a fourteenth aspect, the disclosure provides the health monitoring garment of any of the first through thirteenth aspects, in which the sensor island comprises a rigid spline in alignment with a location of fixation of one or more integrated circuits or sensors to the stretchable circuitry.

In a fifteenth aspect, the disclosure provides the health monitoring garment of any of the first through fourteenth aspects, in which the article of clothing comprises anti-slip material bonded to an interior surface proximal the sensor island within the compression section.

In a sixteenth aspect, the disclosure provides the health monitoring garment of any of the first through fifteenth aspects, in which the article of clothing is a shirt.

In a seventeenth aspect, the disclosure provides the health monitoring garment of the sixteenth aspect, in which the compression section is located across the torso of the shirt such that the sensor island would be positioned in proximity to the left pectoral muscle of the person wearing the article of clothing.

In an eighteenth aspect, the disclosure provides the health monitoring garment of any of the first through seventeenth aspects, in which the health monitoring garment comprises two or more sensor islands.

In a nineteenth aspect, the disclosure provides the health monitoring garment of the eighteenth aspect, in which one sensor island serves as a master sensor island with data from the remaining sensor islands wirelessly transmitted thereto, the master sensor island communicating with an external device.

In a twentieth aspect, the disclosure provides a sensor island for placement in a health monitoring garment. The sensor island comprises two or more sensors, stretchable circuitry, and one or more power supplies, within a self-contained unit. At least one of the two or more sensors comprises a stretchable sensor and the stretchable circuitry comprises a planar, substantially wave-shaped region of flexible circuit board. The sensor island further comprises an encapsulation of the stretchable circuitry and the one or more power supplies with an elastomeric material.

In a twenty-first aspect, the disclosure provides the sensor island of the twentieth aspect, in which the one or more power supplies comprise a rechargeable thin film battery and the sensor island further comprises a wireless charging circuit connected to the rechargeable thin film battery.

In a twenty-second aspect, the disclosure provides the sensor island of the twentieth or twenty-first aspect, in which the sensor island further comprises one or more wireless communication modules within the self-contained unit and encapsulated with the elastomeric material.

In a twenty-third aspect, the disclosure provides the sensor island of any of the twentieth through twenty-second aspects, in which the two or more sensors comprise at least two dry electrodes connected by the stretchable circuitry.

It should be apparent to those skilled in the art that various modifications and variations may be made to the embodiments described within without departing from the spirit and scope of the claimed subject matter. Thus, it is intended that the specification cover the modifications and variations of the various embodiments described within provided such modification and variations come within the scope of the appended claims and their equivalents.

As used throughout, the singular forms "a," "an" and "the" include plural referents unless the context clearly dictates otherwise. Thus, for example, reference to "a" component includes aspects having two or more such components, unless the context clearly indicates otherwise.

Optional or optionally means that the subsequently described event or circumstances may or may not occur. The description includes instances where the event or circumstance occurs and instances where it does not occur.

It should be understood that any two quantitative values assigned to a property or measurement may constitute a range of that property or measurement, and all combinations of ranges formed from all stated quantitative values of a given property or measurement are contemplated in this disclosure.

As used here and in the appended claims, the words "comprise," "has," and "include" and all grammatical variations thereof are each intended to have an open, non-limiting meaning that does not exclude additional elements or steps.

Having described the subject matter of the present disclosure in detail and by reference to specific embodiments thereof, it is noted that the various details disclosed within should not be taken to imply that these details relate to elements that are essential components of the various embodiments described within, even in cases where a particular element is illustrated in each of the drawings that accompany the present description. Further, it should be apparent that modifications and variations are possible without departing from the scope of the present disclosure, including, but not limited to, embodiments defined in the appended claims. More specifically, although some aspects of the present disclosure are identified as particularly advantageous, it is contemplated that the present disclosure is not necessarily limited to these aspects.

What is claimed is:

1. A health monitoring garment comprising:
   an article of clothing comprising at least one compression section to provide a snug fit against a person wearing the article of clothing; and
   a sensor island, wherein
     the sensor island comprises two or more sensors, stretchable circuitry comprising
       a substantially wave-shaped region, and one or more power supplies within a self-contained unit, and
     the sensor island and the compression section comprise fasteners capable of reversible attachment and disengagement of the sensor island from the compression section, wherein:
     at least one of the two or more sensors comprises a stretchable sensor,
     the sensor island further comprises an encapsulation of the stretchable circuitry and the one or more power supplies with an elastomeric material to form encapsulated circuitry, where the substantially wave-shaped region comprises a conductive ink printed on a stretchable elastomer substrate;
     the two or more sensors comprise at least two dry electrodes connected by the stretchable circuitry;
     the stretchable circuitry comprises electrical contacts which are unencapsulated and configured to electrically mate with a mating surface on each of the dry electrodes;
     the dry electrodes each comprise an extended flange around the periphery of the dry electrode, the extended flange and the encapsulated circuitry of the sensor island form a recessed channel sized to engage a mating ring provided within the structure of the compression section of the article of clothing, the mating rings capable of being resiliently stretched in one or more directions where the recessed channel and the mating ring providing the fasteners capable of reversible attachment and disengagement of the sensor island from the compression section; and
     a retention washer threadably affixed to each of the at least two dry electrodes with the encapsulated circuitry captured between the retention washers and the dry electrodes such that the mating surfaces of the dry electrodes are retained in contact with the electrical contacts of the stretchable circuitry.

2. The health monitoring garment of claim 1, wherein the sensor island further comprises one or more wireless communication modules within the self-contained unit and encapsulated with the elastomeric material.

3. The health monitoring garment of claim 1, wherein the elastomeric material comprises silicone.

4. The health monitoring garment of claim 1, wherein the compression section comprises a pocket formed within the article of clothing to house the sensor island, the pocket comprising orifices to allow physical contact between the dry electrodes and the skin of the person wearing the article of clothing.

5. The health monitoring garment of claim 1, wherein the one or more power supplies comprise a thin film battery.

6. The health monitoring garment of claim 5, wherein the thin film battery is a rechargeable thin film battery and the sensor island further comprises a wireless charging circuit connected to the rechargeable thin film battery.

7. The health monitoring garment of claim 1, wherein the one or more sensors further comprise one or more of a heart rate sensor, a sweat sensor, a temperature sensor, a gyroscope, and an accelerometer.

8. The health monitoring garment of claim 1, wherein the stretchable sensor is a respiration sensor.

9. The health monitoring garment of claim 1, wherein the sensor island comprises a rigid spline with one or more integrated circuits or one or more of the sensors connected to the stretchable circuitry in alignment with the rigid spline.

10. The health monitoring garment of claim 1, wherein the article of clothing comprises anti-slip material bonded to an interior surface proximal the sensor island within the compression section.

11. The health monitoring garment of claim 1, wherein the article of clothing is a shirt.

12. The health monitoring garment of claim 11, wherein the compression section is located across the torso of the shirt such that the sensor island would be positioned in proximity to the left pectoral muscle of the person wearing the article of clothing.

13. The health monitoring garment of claim 1, wherein the health monitoring garment comprises two or more sensor islands.

14. The health monitoring garment of claim 13, wherein one sensor island serves as a master sensor island with data from the remaining sensor islands wirelessly transmitted thereto, the master sensor island communicating with an external device.

15. A sensor island for placement in a health monitoring garment, the sensor island comprising:
   two or more sensors, stretchable circuitry, and one or more power supplies, within a self-contained unit, wherein at least one of the two or more sensors comprises a stretchable sensor and the stretchable circuitry comprises a planar, substantially wave-shaped region of flexible circuit board, the planar, substantially wave-shaped region comprising a conductive ink printed on a stretchable elastomer substrate; and
   an encapsulation of the stretchable circuitry and the one or more power supplies with an elastomeric material to form encapsulated circuitry, wherein:
   the two or more sensors comprise at least two dry electrodes connected by the stretchable circuitry;
   the stretchable circuitry comprises electrical contacts which are unencapsulated and configured to electrically mate with a mating surface on each of the dry electrodes;
   the dry electrodes each comprise an extended flange around the periphery of the dry electrode, the extended flange and the encapsulated circuitry of the sensor island form a recessed channel sized to engage a mating ring provided within the structure of the compression section of the article of clothing, the mating rings capable of being resiliently stretched in one or more directions where the recessed channel and the mating ring providing the fasteners capable of reversible attachment and disengagement of the sensor island from the compression section; and
   a retention washer threadably affixed to each of the at least two dry electrodes with the encapsulated circuitry captured between the retention washers and the dry electrodes such that the mating surfaces of the dry electrodes are retained in contact with the electrical contacts of the stretchable circuitry.

16. The sensor island of claim 15, wherein the one or more power supplies comprise a rechargeable thin film battery and the sensor island further comprises a wireless charging circuit connected to the rechargeable thin film battery.

17. The sensor island of claim 15, wherein the sensor island further comprises one or more wireless communication modules within the self-contained unit and encapsulated with the elastomeric material.

18. The health monitoring garment of claim 1, wherein the dry electrode comprises a snap-on connector and the compression section comprises a mating snap-on connector oriented toward an interior of the health monitoring garment, wherein:
   the snap-on connector comprises a recessed groove on the dry electrode, and
   the mating snap-on connector comprises a snap ring comprising a geometry capable of locking into the recessed groove to secure the sensor island in place within the compression section.

19. The health monitoring garment of claim 18, wherein the snap ring and the recessed groove comprise a substantially circular geometry.

20. The health monitoring garment of claim 1, wherein the retention washer comprises one or more orifices disposed around the periphery of the retention washer.

* * * * *